(12) United States Patent
Sinha et al.

(10) Patent No.: US 8,163,891 B2
(45) Date of Patent: Apr. 24, 2012

(54) PROCESS FOR THE PREPARATION OF POLY(ALKOXYLATED) OLIGONUCLEOTIDES

(75) Inventors: Nanda Dulal Sinha, Milford, MA (US); Saied Shaikh, Milford, MA (US); Satya Kuchimanchi, Milford, MA (US)

(73) Assignee: Avecia Biotechnology Inc, Milford, MA (US)

( * ) Notice: Subject to any disclaimer, the term of this patent is extended or adjusted under 35 U.S.C. 154(b) by 438 days.

(21) Appl. No.: 12/086,172

(22) PCT Filed: Nov. 20, 2006

(86) PCT No.: PCT/GB2006/004324
§ 371 (c)(1),
(2), (4) Date: Sep. 22, 2009

(87) PCT Pub. No.: WO2007/066069
PCT Pub. Date: Jun. 14, 2007

(65) Prior Publication Data
US 2010/0029924 A1    Feb. 4, 2010

(51) Int. Cl.
*C07H 15/00* (2006.01)
*C07H 17/00* (2006.01)
*C07G 3/00* (2006.01)
(52) U.S. Cl. ............... 536/18.6; 536/18.5; 536/25.3
(58) Field of Classification Search .......... None
See application file for complete search history.

(56) References Cited

OTHER PUBLICATIONS

Jäschke et al., "Synthesis and properties of oligodeoxyribonucleotide-polyethylene glycol conjugates", Nucleic Acids Research, 22(22):4810-4817 (1994).
Efimov et al., "Dipentafluorophenyl carbonate—a reagent for the synthesis of oligonucleotides and their conjugates", Nucleic Acids Research, 21(23:5337-5344 (1993).
Jäschke et al., "Automated Incorporation of Polyethylene Glycol into Synthetic Oligonucleotides", Tetrahedron Letters, 34(2):301-304 (1993).
Manoharan et al., "Oligonucleotide Conjugates: Alteration of the Pharmacokinetic Properties of Antisense Agents", Nucleosides & Nucleotides, 14(3-5):969-973 (1995).
Rahman et al., "Antibacterial Activity and Inhibition of Protein Synthesis in *Escherichia coli* by Antisense DNA Analogs", Antisense Research and Development, 1:319-327 (1991).
Zalipsky et al., "Use of Functionalized Poly(Ethylene Glycol)s for Modification of Polypeptides", Poly(Ethylene Glycol) Chemistry: Biotechnical and Biomedical Applications, pp. 347-370 (1992).

*Primary Examiner* — Patrick Lewis
(74) *Attorney, Agent, or Firm* — Timothy E. Tinkler

(57) ABSTRACT

A process for the preparation of a poly(alkoxylated) oligonucleotide is provided. The process comprises reacting an oligonucleotide which has been purified by ultrafiltration with a poly(alkoxide) thereby to form a poly(alkoxylated) oligonucleotide. The poly(alkoxyalted) oligonucleotide may be separated from non-poly(alkoxyalted) oligonucleotide by ultrafiltration under denaturing conditions, such as the presence of organic solvents, for example, ethanol; the presence of urea; the addition of chaotropic salts, for example perchlorate and guanidinium salts; the presence of formamide; and the application of heat, for example a temperature of up to about 70° C.

18 Claims, No Drawings

PROCESS FOR THE PREPARATION OF POLY(ALKOXYLATED) OLIGONUCLEOTIDES

The present invention concerns a process for the preparation of oligonucleotide derivatives, and particularly poly(alkoxylated) oligonucleotides.

Poly(alkoxylated) oligonucleotides, especially poly(ethylene glycol) oligonucleotides, have been proposed for improving the bioavailability, nuclease resistance and pharmacokinetic properties of oligonucleotides. Such compounds are commonly prepared by a process comprising the assembly of a desired oligonucleotide; introducing a reactive site, commonly by reaction of a linker comprising an amino or thiol moiety with a free 5'-hydroxy group of the oligonucleotide; and reacting the oligonucleotide with a mono-protected poly(alkylene glycol). The oligonucleotides employed in this process are commonly employed without full purification, or are purified by chromatography. Surprisingly, it has now been found that an improved process for the preparation of poly(alkoxylated) oligonucleotides is achieved, giving higher yields and increased simplicity of operation, where the oligonucleotide has been purified by ultrafiltration prior to derivatization with the poly(alkoxide).

According to a first aspect of the present invention, there is provided a process for the preparation of a poly(alkoxylated) oligonucleotide which comprises reacting an oligonucleotide with a poly(alkoxide) thereby to form a poly(alkoxylated) oligonucleotide, characterized in that the oligonucleotide employed has been purified by ultrafiltration.

Oligonucleotides which can be derivatized by the process of the present invention include nucleic acids containing natural sugar moieties, for example 2'-deoxyribonucleic acids (hereinafter "DNA") and ribonucleic acids (hereinafter "RNA") and nucleic acids containing modified sugar moieties, modified phosphate moieties, or modified nucleobases. Modification to the sugar moiety includes replacing the ribose ring with an alternative ring, such as a hexose, cyclopentyl or cyclohexyl ring, or employing an acyclic sugar. Alternatively, the D-ribose ring of a naturally occurring nucleic acid can be replaced with an L-ribose ring or the β-anomer of a naturally occurring nucleic acid can be replaced with the α-anomer. The oligonucleotide may also comprise one or more abasic moieties. Modified phosphate moieties include phosphorothioates, phosphorodithioates, methyl phosphonates, methyl phosphates, phosphoramidates and phosphorthioamidates. Chimeric oligonucleotides comprising mixtures of two or more of the foregoing may be prepared, for example, oligonucleotides comprising mixtures of deoxyribo- and ribonucleosides, particularly mixtures of deoxyribonucleosides and 2'-substituted nucleosides, such as 2'-O-methyl and 2'-O-methoxyethylribonucleosides or 2'-fluoronucleosides, and oligonucleotides that comprise both phosphodiester and phosphorothioate linkages. Examples of oligonucleotides comprising mixtures of nucleosides include ribozymes and aptamers. In many embodiments, the oligonucleotide derivatized has from 2 to about 100 nucleobases, more preferably from 2 to about 75 nucleobases, and most preferably from 8 to 40 nucleobases.

Preferred oligonucleotides which can be derivatized by the process of the present invention are of Formula (1):

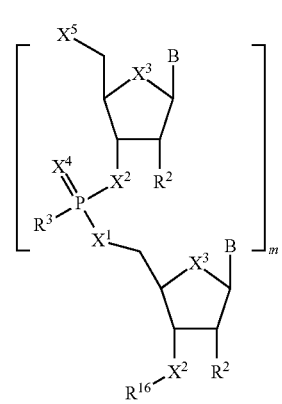

Formula (1)

In Formula (1), $X^1$ for each occurrence is, independently, —O— or —S—. Preferably, X' is —O— at every occurrence. $X^2$ for each occurrence is, independently, —O—, —S—, or —NR—, wherein R is H or an alkyl, such as a $C_{1-4}$ alkyl, group. Preferably, $X^2$ is —O— at every occurrence. $X^3$ for each occurrence is, independently, —O—, —S—, —CH$_2$—, or —(CH$_2$)$_2$—. Preferably, $X^3$ is —O— at every occurrence. In a most preferred embodiment, $X^1$, $X^2$, and $X^3$ are all —O— at every occurrence. $X^4$ for each occurrence is, independently, O or S. $X^5$ is —OH, —NH$_2$, —SH, or preferably a linker comprising an —NH$_2$ or —SH group. $R^2$ for each occurrence is, independently, —H, —F, —OR$^6$, —NR$^7$R$^8$, —SR$^9$, or a substituted or unsubstituted aliphatic group, such as methyl or allyl. Preferably, $R^2$ for each occurrence is, independently, —H, —F or —OR$^6$. $R^3$ for each occurrence is, independently, a substituted or unsubstituted aliphatic group, —OR$^{10}$, —SR$^{10}$, or, preferably O$^-$M$^+$ or S$^-$M$^+$, where M$^+$ is a counter ion, commonly an alkali metal cation, and preferably Na$^+$. $R^6$ for each occurrence is, independently, —H, a substituted or unsubstituted aliphatic group (e.g., methyl, ethyl, methoxyethyl or allyl), a substituted or unsubstituted aryl group, a substituted or unsubstituted aralkyl, an alcohol protecting group, or —(CH$_2$)$_q$—NR$^{18}$R$^{19}$. $R^7$ and $R^8$ for each occurrence are each, independently, —H, a substituted or unsubstituted aliphatic group, or an amine protecting group. Alternatively, $R^7$ and $R^8$ taken together with the nitrogen to which they are attached are a heterocyclyic group. $R^9$ for each occurrence is, independently, —H, a substituted or unsubstituted aliphatic group, or a thio protecting group. $R^{10}$ is for each occurrence is, independently, a substituted or unsubstituted aliphatic group, a substituted or unsubstituted aryl group or a substituted or unsubstituted aralkyl group, preferably —CH$_2$CH$_2$CN, —CH$_2$CH$_2$—Si(CH$_3$)$_2$C$_6$H$_5$, —CH$_2$CH$_2$—S(O)$_2$—CH$_2$CH$_3$, —CH$_2$CH$_2$—C$_6$H$_4$—NO$_2$ and most preferably —CH$_2$CH$_2$CN. $R^{18}$ and $R^{19}$ are each, independently, —H, a substituted or unsubstituted aryl group, a substituted or unsubstituted heteroaryl group, a substituted or unsubstituted aliphatic group, a substituted or unsubstituted aralkyl group, a substituted or unsubstituted heteroaralkyl group or an amine protecting group. Alternatively, $R^{18}$ and $R^{19}$ taken together with the nitrogen to which they are attached form a heterocyclic group. q is an integer from 1 to about 6. B is —H or an optionally protected natural or unnatural nucleobase. $R^{16}$ is H, a hydroxyl protecting group, a thio protecting group, an amino protecting group or a group of formula —(CH$_2$)$_q$—NR$^{18}$R$^{19}$ as described above. m is a positive integer, commonly from 1 to 99, such as from 1 to 74, and preferably from 7 to 39. In many preferred embodiments, the oligonucleotide is fully deblocked.

When $X^5$ represents —OH, such a group is normally formed by conventional oligonucleotide synthesis employing 5'-O-protected nucleosides, such as 5'-O-dimethoxytrityl nucleosides, the —OH groups being formed during cleavage and deprotection.

When $X^5$ represents —NH$_2$ or —SH, such groups can be introduced by the use of a 5'-protected amino or protected thio nucleoside as the 5'-terminal nucleoside in the synthesis, with the —NH$_2$ or —SH groups being formed during cleavage and deblock. Examples of protecting groups for NH$_2$ groups are well known in the art, and include trifluoroacetyl, FMOC and trityl, especially monomethoxytrityl, groups. Examples of protecting groups for SH groups are well known in the art, and include particularly trityl, especially dimethoxytrityl, groups, and protecting groups which form a disulfide group, such as an alkyldisulfide group.

When $X^5$ represents a linker comprising an —NH$_2$ or —SH group, such linkers are commonly introduced as part of the oligonucleotide assembly process as the final step prior to cleavage and deprotection. The linker is typically coupled to a free 5'-terminal hydroxy group on the nascent oligonucleotide. The linker employed is commonly a compound comprising a first group which will react with the oligonucleotide, preferably with a free hydroxy group, the linker also comprising a second group for attachment to a poly(alkoxide), the second group being separated from the first group by a spacer group.

Examples of the first group which will react with the oligonucleotide include imide, aldehyde, carboxyl, isothiocyanate, halogen groups, and preferably phosphoramidite groups, most preferably N,N-diisopropyl betacyanoethyloxyphosphoramidite groups. When a phosphoramidite group is employed, it is preferably oxidized or sulphurized after attachment to the oligonucleotide to form a phosphate or phosphorothioate triester, and subsequently a phosphate or phosphorothioate diester after cleavage and deblocking.

It will be recognized that the nature of the second group for attachment to the poly(alkoxide) will be chosen depending upon the nature of the poly(alkoxide) with which it is desired to react. In many embodiments, the second group which will react with the poly(alkoxide) comprises a reactive amino or thiol group, commonly employed in protected form during coupling of the linker to the oligonucleotide, which, after deprotection can react with an appropriately functionalized poly(alkoxide), for example an activated ester-, such as N-hydroxysuccinimide- ("NHS") or maleimide-, functionalized poly(alkoxides). Examples of spacers are poly(alkylene) chains, for example $C_{2-15}$ chains. In certain embodiments, the polyalkylene chain can comprise one or more heteroatoms, commonly only 1 heteroatom, in the chain, such as an oxygen atom forming an ether linkage. Examples of linkers are succinimidyl maleimidomethyl cyclohexane carboxylate; succinimidyl pyridyl dithiopropionate; phenylene diisothiocyanate and disuccinimidyl suberate.

Methods of preparing oligonucleotides are well known in the art. In many embodiments, the oligonucleotide will be prepared by the phosphoramidite method, wherein the oligonucleotide is assembled by sequential coupling of protected nucleoside phosphoramidites to a nascent oligonucleotide. Once the desired oligonucleotide sequence is assembled, the oligonucleotide is deprotected and cleaved from the solid support. The oligonucleotide may then be purified by, for example, precipitation or chromatography.

The synthesis of the oligonucleotide commonly involves the use of ammonia and/or amines and ammonium salts, especially $C_{1-4}$ alkyl amines and ammonium salts. For example, the synthesis of ribonucleotides often employs one or more of ammonia, methylamine, triethylammonium hydrofluoride and tetrabutylammonium fluoride. Such amines and salts, along with other organic reagents and small fragments from the synthesis may not be adequately removed by precipitation or chromatography, even if such purifications are attempted.

Even if previous purifications, such as chromatography or precipitation have been attempted, in the process of the first aspect of the present invention, the oligonucleotide is purified by ultrafiltration prior to poly(alkoxylation). Ultrafiltration is carried out by passing a solution of the oligonucleotide through an ultrafiltration membrane, whereby lower molecular weight impurities, such as alkyl ammonium salts and solvents which may be present as residues from the synthesis and cleavage and deprotection, pass through the membrane, with the oligonucleotide being retained without passing through the membrane. The ultrafiltration serves to reduce the ratio of lower molecular weight impurities to oligonucleotide. The ultrafiltration can be operated in such a way so as to increase the concentration of the oligonucleotide in solution, by not adding fresh solvent (commonly water) to replace the volume passing through the ultrafiltration membrane, or by adding less water than the volume passed through. Alternatively, an equivalent or greater volume of solvent than that passed through the membrane can be added. The solution is commonly forced through the ultrafiltration membrane by the use of increased pressure.

The ultrafiltration step is preferably carried out in the presence of an aqueous sodium salt solution, most preferably sodium chloride solution, in order to effect formation of the oligonucleotide in the desired sodium salt form, and to displace any residual ammonium, including alkylammonium, ions.

A plurality of ultrafiltration steps may be carried out if desired. In many embodiments, the final ultrafiltration step or steps comprise ultrafiltration in the presence of purified water, particularly following an ultrafiltration step in the presence of sodium salts. Ultrafiltration with purified water is commonly carried out until the oligonucleotide is substantially free from ammonium and residual inorganic sodium salts. Preferably, concentrations of residual inorganic sodium salts are reduced to levels below about 100 pmm, most preferably below about 50 ppm, such as from 30 to 50 ppm. Concentrations of residual ions are often monitored by conductivity measurement, with values of less than 75 microsiemens/cm, such as from 30 to 50 microsiemens/cm being preferred in the final permeate.

Ultrafiltration membranes which can be employed have a molecular weight cut-off selected to be lower than the molecular weight of the oligonucleotide. In embodiments where it is desired to remove alkylammonium ions from the solution, a molecular weight cut off higher than that of the alkylammonium ions is employed. In many embodiments, for example with a typical 15 to 40 mer oligonucleotide having a molecular weight of approximately 4.5 to 12 kD, a molecular weight cut off in the range of from 1 kD to 3 kD is employed.

The process according to the present invention is often carried out at a temperature in the range of from 0° C. to about 50° C., and preferably at ambient temperature, such as from about 15° C. to about 30° C.

When increased pressure is employed, it will be recognized that the actual upper limit of the pressure that can be employed will be determined by the ability of the membrane to maintain its integrity under such pressures. In many embodiments, pressures of up to 60 bar, especially up to 50 bar, and particularly pressures in the range of from 15 to 35 bar, such as about 30 bar, can be employed.

The oligonucleotide can be poly(alkoxylated) using methods known in the art. In many embodiments, the poly(alkoxylation) is achieved by reaction between a poly(alkyleneoxide) which has been functionalized in order to react with the oligonucleotide. In preferred embodiments, where the oligonucleotide comprises a linker having a reactive amino or thio group, the poly(alkyleneoxide) is functionalized with an activated ester group, such as NHS, which is often employed where the linker comprises a reactive amino group, or a maleimide group which is often employed where the linker comprises a reactive thiol group.

Poly(alkoxides) which can be employed in the present invention include poly(ethylene oxides), poly(propylene oxides) and mixed poly(ethylene oxide)/poly(propylene oxide) compounds. The poly(alkoxides) preferably are of the formula: $P'O-(CH_2CH_2O-)_x-(CH_2CHRO-)_y-(CH_2CH_2O-)_zQ$, wherein x, y and z are independently zero or positive integers, provided that at least one of x, y and z is not zero; R is H or an alkyl, such as a $C_{1-4}$ alkyl, particularly a methyl, group, P' is a capping group or a labelling group, and Q is a group permitting coupling with the oligonucleotide. When x, y or z are not zero, they are typically up to 1000. In some embodiments, x is from 3 to 1000, for example from 100 to 500, and both y and z are zero. In other embodiments, x and y are independently from 3 to 1000, for example from 100 to 500, and z is zero. In yet other embodiments, x and z are independently from 3 to 500, for example from 100 to 300, and y is from 3 to 1000, for example from 100 to 500. Preferably, the poly(alkyleneoxide) is capped, for example by a $C_{1-4}$ alkyl, especially a methyl, group. Labelling groups which may be represented by P' include fluorescein and biotin.

The poly(alkoxide) compounds employed are commonly identified by their approximate average molecular weight and abbreviated chemical name (for example PEG=poly(ethylene glycol); PPG=poly(propylene glycol). The poly(alkyleneoxide) may be linear or branched, and commonly has an average molecular weight of from 0.2 kD to 60 kD, for example from 2 kD to 40 kD. When the poly(alkylene oxide) is branched, the group, Q, permitting coupling with the oligonucleotide may carry two or more poly(alkylene oxide) chains. For example, Q may represent a lysine or equivalent moiety carrying two poly(alkylene oxide) chains, and an activated ester, especially an NHS group. Preferably, the poly(alkoxide) is PEG.

The reaction between the oligonucleotide and the poly(alkylene oxide) preferably takes place in an aqueous organic solvent comprising water and a water miscible organic solvent which does not interfere with the coupling between the oligonucleotide and the poly(alkylene oxide). Preferred organic solvents include acetonitrile and dimethylformamide. The oligonucleotide is commonly employed as an aqueous solution in a buffer, such as a sodium bicarbonate or sodium borate buffer, commonly having a pH in the range of from 8.3 to 9.5, with the poly(alkylene oxide) employed as a solution in the water miscible organic solvent. Relative volumes and concentrations are selected such that the oligonucleotide and poly(alkylene oxide) remain in solution during the reaction. In many embodiments, the concentration of organic solvent is up to about 20% to 50% v/v. Mole ratios of oligonucleotide to poly(alkylene oxide) are commonly from about 1:1 to about 1:1.5. Addition of poly(alkylene oxide) to oligonucleotide preferably continues until completion of the reaction, conveniently monitored by HPLC. In many embodiments, a reaction temperature of from ambient to about 40° C. is employed, such as from about 35 to 40° C.

Following the preparation of a product poly(alkoxylated) oligonucleotide, the product is preferably separated from any unreacted oligonucleotide. Surprisingly, it has been found that this separation is advantageously achieved by the use of ultrafiltration under denaturing conditions. Accordingly, a second aspect of the present invention provides a process for the separation of a poly(alkoxylated) oligonucleotide, from a non-poly(alkoxylated) oligonucleotide, which comprises the ultrafiltration of a mixture of a poly(alkoxylated) oligonucleotide and non-poly(alkoxylated) oligonucleotide under denaturing conditions.

Poly(alkoxylated) oligonucleotides and oligonucleotides employed in the process of the second aspect of the present invention are as described for the first aspect of the present invention.

The ultrafiltration is commonly carried out by passing a solution of poly(alkoxylated) oligonucleotide and oligonucleotide through an ultrafiltration membrane using apparatus known in the art, such that the non-poly(alkoxylated) oligonucleotide is passes through the membrane, and the poly(alkoxylated) oligonucleotide is retained. Thereby, the ratio of poly(alkoxylated) oligonucleotide to non-poly(alkoxylated) oligonucleotide in the retentate is increased.

Denaturing conditions are those which cause a breakdown in the secondary structure of the poly(alkoxylated) oligonucleotide and non-poly(alkoxylated) oligonucleotide, and will be readily apparent to one of ordinary skill in the art for a given poly(alkoxylated) oligonucleotide and non-poly(alkoxylated) oligonucleotide mixture. In many embodiments, preferred denaturing conditions include the presence of organic solvents, for example, ethanol; the presence of formamide; the presence of urea; the addition of chaotropic salts, for example perchlorate and guanidinium salts; and the application of heat, for example a temperature of up to about 70° C.

The ultrafiltration employs an ultrafiltration membrane with a molecular weight cut-off selected according to the molecular weights of the poly(alkoxylated) oligonucleotide and the non-poly(alkoxylated) oligonucleotide. The molecular weight cut-off is selected to be higher than the molecular weight of the non-poly(alkoxylated) oligonucleotide, but lower than the molecular weight of the poly(alkoxylated) oligonucleotide. For example, where the oligonucleotide has a molecular weight of approximately 4.5 to 12 kD, and where the poly(alkoxide) with a molecular weight of >35 kD, an ultrafiltration membrane having a molecular weight cut off in the range of from 15 kD to 30 kD may conveniently be employed.

A third aspect of the present invention comprises a process for preparing a purified poly(alkoxylated) oligonucleotide, which comprises:

a) preparing a poly(alkoxylated) oligonucleotide by a process according to the first aspect of the present invention; and
b) separating the poly(alkoxylated) oligonucleotide from non-poly(alkoxylated) oligonucleotide by a process according to the second aspect of the present invention.

The present invention is illustrated without limitation by the following examples.

1. Conjugation of PEG with Oligonucleotide

A crude 5'-pentylamino-modified chimeric phosphate oligonucleotide having a molecular weight of 9200 was prepared by conventional phosphoramidite chemistry using an AKTA synthesizer (commercially available from GE Healthcare). Cleavage and deprotection were achieved with methanolic ammonia, with alkylsilyl protecting groups being removed using tetrabutylammonium fluoride solution. The cleaved oligonucleotide was quenched by treatment with alkaline buffer, the pH adjusted to ca. 7, and a solution of the oligonucleotide in water for injection ("WFI") was prepared. A 90 ml aliquot (230 micromoles; 30,240 OD units) was taken and to this was added sodium borate ($Na_2B_4O_3$; 3.43 g) followed by sodium chloride (10.4 g). The total volume was raised to 1 L by the addition of WFI. This solution was thoroughly mixed by sonication for 10 mins, and stored at room temperature for 60 mins.

A 1 kD molecular weight cut-off Centramate™ ultrafiltration membrane (available from Pall Filtron) was washed with 4 L of WFI. Ultrafiltration of the crude oligonucleotide solution was performed in a Pall Filtron TFF system. Initial desalting was achieved by adding 4 L of WFI and pumping the solution through the TFF system to achieve a retentate volume of 250 ml. 4 L of 1M NaCl solution was added in 4×750 ml and 1×1 L increments and ultrafiltration to a retentate volume of 250 ml carried out after each addition. Subsequently, WFI was added and ultrafiltration continued until the conductivity of the retentate was reduced to 30 microsiemens/cm, and the retentate concentrated to a volume of 250 mL. The TFF system was thoroughly washed with WFI to give a final 360 ml of oligonucleotide solution. The concentration of the solution was 83 OD/ml, yielding a total of 29880 OD units of sodium-salt exchanged oligonucleotide from 30240 OD units.

The resulting oligonucleotide was then lyophilized and reconstituted in borate buffer (14.8 ml; 0.5M; pH9.3). PEG NHS ester (PEG mol. wt. 40000; 3.67 g) in acetonitrile (12 ml) was added and the reaction allowed to proceed at room temperature until HPLC indicated that the reaction was complete. Quenching was carried out by the addition of water. The crude PEG-oligonucleotide conjugate was split into two parts, A (14750 OD units) and B (13000 OD units).

Part A was purified as follows. 14750 OD units containing ~7500 OD units of desired conjugate (the remainder of the material being unreacted oligonucleotide and related impurities, hydrolyzed PEG derivatives and other reagents) was purified on a Source 15Q ion exchange column (100 mL resin, 5 cm diameter). The concentration of the crude conjugate was adjusted with water and 20% ethanol to ~600 OD/ml. The product was eluted using a linear gradient (0 to 40% B in 20 column volumes) consisting of Buffer A: 25 mM Tris, 10 mM NaCl; buffer B: 25 mM Tris containing 1M NaCl. From this purification, 6600 OD units of conjugate (yield=88%) was isolated, with a purity of 84%.

Part B was purified as follows. 13000 OD units of conjugate was processed by ultrafiltration using the Pall Filtron TFF system under denaturing conditions, to remove unreacted oligonucleotide and related impurities from the conjugation reaction. For the denaturing process, the crude conjugate was diluted to 1 L using $NaClO_4$ to give a final concentration of 1M. This solution was heated at 42° C. for 2 h, and then subjected to ultrafiltration using a Pall Filtron Centramate, 30 kD mw cut-off and the retentate concentrated to 200 mL. A further three cycles of ultrafiltration were carried out by diluting the retentate with aqueous sodium perchlorate (1M) to a total volume of 1 L then repeating the step. On the final cycle, the retentate was concentrated to 200 mL, then diluted again with WFI (1 L) and again subjected to ultrafiltration. This procedure was repeated a further seven times to ensure removal of sodium perchlorate salts. 6860 OD units of semi-purified conjugate was recovered. The semi-purified conjugate was purified by ion exchange chromatography using Source 15Q resin (Tris, NaCl buffer, linear gradient of 0 to 40% B in 20 column volumes) and yielded 4200 OD units of purified conjugate (65% yield) with a purity of 91%

2. Purification and Isolation of the PEG-Oligonucleotide Conjugate Using UF for the Separation of PEG-Oligonucleotide from Non-PEG-Oligonucleotide A 5'-pentylamino-modified chimeric phosphate oligonucleotide having a molecular weight of 9200, reconstituted in borate buffer (0.5M; pH9.3) was reacted with PEG NHS ester (PEG mol. wt. 40000) in acetonitrile, and the reaction allowed to proceed at room temperature until HPLC indicated that the reaction was complete. Quenching was carried out by the addition of water. The crude reaction mixture was added to aqueous sodium perchlorate (1M; 1800 mL) and the solution mixed at 42° C. for 1.5 h. Ultrafiltration, to remove non-PEG oligo, was then carried out using a Pall Filtron Centramate, 30 kD mw cut-off and the retentate concentrated to 600 mL. A further three cycles of ultrafiltration were carried out by diluting the retentate with aqueous sodium perchlorate (550 mM) to a total volume of 2 L then repeating the step. On the final cycle, the retentate was concentrated to 1 L then diluted again with WFI (1 L) and again subjected to ultrafiltration. This procedure was repeated a further seven times to ensure removal of sodium perchlorate salts. The retentate from this process contained 74,000 OD (260 nm) of oligonucleotide. This material was freeze dried then the bulk of it re-dissolved in 250 mL of water-ethanol solution (4:1 v/v). A proportion of this material (ca. 68,000 OD 260 nm) was then purified by ion-exchange HPLC (Source 15Q; eluent 25 mM Tris(aq) with 1M NaCl (aq)). Pooling of the appropriate fractions gave the desired PEG-conjugated oligonucleotide (59820 OD units at 260 nm) at a purity of 95.6% by IEX analysis.

The invention claimed is:

1. A process for the preparation of a poly(alkoxylated) oligonucleotide which comprises reacting an oligonucleotide with a poly(alkoxide) thereby to form a poly(alkoxylated) oligonucleotide, wherein the oligonucleotide employed has been purified by ultrafiltration.

2. A process according to claim 1, wherein the ultrafiltration is carried out in the presence of a sodium salt solution.

3. A process according to claim 2, wherein the final ultrafiltration step or steps comprise ultrafiltration in the presence of purified water, carried out until the oligonucleotide is substantially free from ammonium and residual inorganic sodium salts.

4. A process according to claim 3, wherein the concentration of residual sodium ions is reduced to less than 100 parts per million.

5. A process according to claim 3, wherein the process is carried out to produce a final permeate having a conductivity of less than 75 microsiemens/cm.

6. A process according to claim 1, wherein the oligonucleotide has a molecular weight of approximately 4.5 to 12 kD, and an ultrafiltration membrane having a molecular weight cut off in the range of from 1 kD to 3 kD is employed.

7. A process for the separation of a poly(alkoxylated) oligonucleotide, from a non-poly(alkoxylated) oligonucleotide, which comprises the ultrafiltration of a mixture of a poly(alkoxylated) oligonucleotide and non-poly(alkoxylated) oligonucleotide under denaturing conditions.

8. A process according to claim 7, wherein the denaturing conditions are selected from the group consisting of a) the presence of organic solvents b) the presence of urea; c) the addition of chaotropic salts; d) the presence of formamide; and e) the application of heat.

9. A process according to either of claims 7 and 8, wherein the oligonucleotide has a molecular weight of approximately 4.5 to 12 kD, the poly(alkoxide) has a molecular weight of >35 kD, and an ultrafiltration membrane having a molecular weight cut off in the range of from 15 kD to 30 kD is employed.

10. A process for preparing a purified poly(alkoxylated) oligonucleotide which comprises:
   a) preparing a poly(alkoxylated) oligonucleotide by a process which comprises reacting an oligonucleotide with a poly(alkoxide) thereby to form a poly(alkoxylated) oligonucleotide, wherein the oligonucleotide employed has been purified by ultrafiltration; and
   b) separating the poly(alkoxylated) oligonucleotide from non-poly(alkoxylated) oligonucleotide by a process which comprises the ultrafiltration of a mixture of a poly(alkoxylated) oligonucleotide and non-poly(alkoxylated) oligonucleotide under denaturing conditions.

11. A process according to claim 3, wherein the ultrafiltration is carried out in the presence of a sodium salt solution, and the concentration of residual sodium ions is reduced to from 30 to 50 parts per million.

12. A process according to claim 3, wherein the ultrafiltration is carried out in the presence of a sodium salt solution, and the process is carried out to produce a final permeate having a conductivity of from 30-50 microsiemens/cm.

13. A process according to either of claim 11 or 12, wherein the oligonucleotide has a molecular weight of approximately 4.5 to 12 kD, and an ultrafiltration membrane having a molecular weight cut off in the range of from 1 kD to 3 kD is employed.

14. A process according to claim 7, wherein the denaturing conditions are selected from the group consisting of a) the presence of ethanol; b) the addition of perchlorate or guanidinium salts; and c) heating to a temperature up to about 70° C.

15. A process according to claim 10, wherein the ultrafiltration in step a) is carried out in the presence of a sodium salt solution and until the concentration of residual sodium ions is reduced to from 30 to 50 parts per million.

16. A process according to claim 10, wherein the ultrafiltration in step a) is carried out in the presence of a sodium salt solution and to produce a final permeate having a conductivity of from 30-50 microsiemens/cm.

17. A process according to claim 10, wherein the denaturing conditions in step b) are selected from the group consisting of a) the presence of organic solvents; b) the presence of urea; c) the addition of chaotropic salts; d) the presence of formamide; and e) the application of heat.

18. A process according to any one of claim 10, 15, 16 or 17, wherein the oligonucleotide has a molecular weight of approximately 4.5 to 12 kD, the poly(alkoxide) has a molecular weight of >35 kD, an ultrafiltration having a molecular weight cut off in the range of from 1 kD to 3 kD is employed in step a), and an ultrafiltration membrane having a molecular weight cut off in the range of from 15 kD to 30 kD is employed in step b).

* * * * *

Disclaimer

8,163,891 B2 — Nanda Dulal Sinha, Milford, MA (US); Saied Shaikh, Milford, MA (US); and Satya Kuchimanchi, Milford, MA (US). PROCESS FOR THE PREPARATION OF POLY(ALKOXYLATED) OLIGONUCLEOTIDES. Patent dated April 24, 2012. Disclaimer filed February 12, 2015, by the assignee, Nitto Denko Avecia, Inc.

Hereby disclaims the entire term of said patent.

(Official Gazette, April 7, 2015)